(12) United States Patent
Yamada et al.

(10) Patent No.: US 10,300,177 B2
(45) Date of Patent: May 28, 2019

(54) STORAGE CONTAINER

(71) Applicant: DAIKEN MEDICAL CO., LTD., Osaka-shi, Osaka (JP)

(72) Inventors: Keiichi Yamada, Osaka (JP); Zhonghuan Shen, Osaka (JP); Kazuki Ishibashi, Osaka (JP); Masayuki Uruma, Osaka (JP)

(73) Assignee: DAIKEN MEDICAL CO., LTD., Osaka-Shi, Osaka (JP)

( * ) Notice: Subject to any disclaimer, the term of this patent is extended or adjusted under 35 U.S.C. 154(b) by 363 days.

(21) Appl. No.: 15/104,534

(22) PCT Filed: Dec. 19, 2014

(86) PCT No.: PCT/JP2014/083796
§ 371 (c)(1),
(2) Date: Jun. 15, 2016

(87) PCT Pub. No.: WO2015/098778
PCT Pub. Date: Jul. 2, 2015

(65) Prior Publication Data
US 2016/0317723 A1    Nov. 3, 2016

(30) Foreign Application Priority Data

Dec. 27, 2013 (JP) ................................ 2013-270728

(51) Int. Cl.
*A61M 1/00* (2006.01)

(52) U.S. Cl.
CPC ........ *A61M 1/0013* (2013.01); *A61M 1/0001* (2013.01); *A61M 1/0025* (2014.02);
(Continued)

(58) Field of Classification Search
CPC . A61M 1/0013; A61M 1/0025; A61M 1/0001
See application file for complete search history.

(56) References Cited

U.S. PATENT DOCUMENTS 3,363,627 A   1/1968   Bidwell et al.
3,381,687 A   5/1968   Andersen et al.
(Continued)

FOREIGN PATENT DOCUMENTS

CN    203090020 U    7/2013
EP    0096195 A1    12/1983
(Continued)

OTHER PUBLICATIONS

European Search Report dated Nov. 22, 2016.
Chinese Office Action dated Apr. 21, 2017.
International Search Report.

*Primary Examiner* — Kai Weng
(74) *Attorney, Agent, or Firm* — Gerald E. Hespos; Michael J. Porco; Matthew T. Hespos

(57) ABSTRACT

A storage container includes a storing section including a storage space and an inflow port, and a water sealing section. The storing section includes an inflow section connectable to a tube and a volume changing section capable of changing the volume of the storage space. The volume changing section is deformed to increase the volume of the storage space when pressure in the storage space is about to rise to be equal to or higher than a reference pressure set in advance and is deformed to reduce the volume of the storage space when the pressure in the storage space is about to drop to be lower than the reference pressure.

4 Claims, 11 Drawing Sheets

(52) U.S. Cl.
CPC .............. *A61M 2205/3331* (2013.01); *A61M 2210/101* (2013.01)

(56) References Cited

U.S. PATENT DOCUMENTS

| | | |
|---|---|---|
| 4,018,224 A | 4/1977 | Kurtz et al. |
| 4,544,370 A | 10/1985 | Elliott |
| 5,114,416 A | 5/1992 | Karwoski |
| 7,354,427 B2 * | 4/2008 | Fangrow .............. A61J 1/2089 222/386.5 |

FOREIGN PATENT DOCUMENTS

| | | |
|---|---|---|
| JP | 51-58916 | 5/1976 |
| JP | 57-174802 | 11/1982 |
| JP | 62-153401 | 9/1987 |
| JP | 7-213599 | 8/1995 |
| JP | 2008284138 A | 11/2008 |

\* cited by examiner

STORAGE CONTAINER

TECHNICAL FIELD

The present invention relates to a storage container provided halfway in a suction line for sucking gas and liquid in a body cavity such as the thoracic cavity.

BACKGROUND ART

There have been known storage containers for medical use for storing liquid (blood, etc.) sucked out from the thoracic cavity together with gas that has leaked from the lungs to the thoracic cavity of a patient. For example, Japanese Unexamined Patent Publication No. H07-213599 discloses a storage container including a liquid collecting section including a storage space for storing liquid, a suction-pressure setting section including a suction space connected to a suction pump, and a water sealing section provided between the liquid collecting section and the suction-pressure setting section. In the liquid collecting section, an inflow port for causing liquid and gas in the body cavity of the patient to flow into the liquid collecting section via a tube inserted into the body cavity is provided. The pressure in the suction space is adjusted according to an injection amount of sterile water into the suction-pressure setting section. In an upper part of the suction-pressure setting section, an opening for taking air on the outside into the suction-pressure setting section is provided. The air flows into the suction-pressure setting section through the opening, whereby the pressure in the suction space is maintained constant. The water sealing section is capable of sealing the storage space and the suction space off from each other with the sterile water. The water sealing section is provided for the purpose of, for example, preventing counterflow of outside air into the patient through the suction space and the storage space when the pressure in the storage space drops below the pressure in the suction space.

When the suction pump is driven in a state in which the tube has been inserted into the body cavity of the patient, the liquid and the gas in the body cavity of the patient flow into the liquid collecting section via the inflow port. The liquid that has flowed into the liquid collecting section is stored in a bottom section of the liquid collecting section. On the other hand, the gas that has flowed into the liquid collecting section changes to air bubbles and passes through the sterile water in the water sealing section and is thereafter discharged from the storage container through the suction space.

In a case where the liquid and the gas in the body cavity are sucked using the storage container, if a large amount of gas, i.e. equal to or more than an amount of gas in a steady state, temporarily flows into the liquid collecting section because, for example, the patient coughs, a state of the liquid collecting section changes to an excessive positive pressure state. In the excessive positive pressure state, it is difficult for the patient to inflate the lungs (breathe). Therefore, a positive-pressure relief valve for avoiding the excessive positive pressure state is provided in the liquid collecting section of the storage container. That is, when a large amount of gas temporarily flows into the liquid collecting section, the positive-pressure relief valve opens, whereby excess gas is discharged from the storage space to the outside of the storage container. As a result, although the state of the liquid collecting section is suppressed from changing to the excessive positive pressure state, since a total amount of the gas in the body cavity or the liquid collecting section decreases, the state of the liquid collecting section changes to an excessive negative pressure state according to subsequent breathing of the patient. In the excessive negative pressure state, a large load is applied to the lungs. Therefore, in the storage container, a one-way valve for avoiding the excessive negative pressure state of the liquid collecting section is provided. The one-way valve is provided in a partition wall in the water sealing section, which wall defines the storage space and the suction space. The one-way valve allows only passage of the gas from the suction space to the storage space. That is, after the gas is discharged from the liquid collecting section to the outside via the positive-pressure relief valve, the one-way valve opens when the pressure of the liquid collecting section drops according to the breathing of the patient, and as a consequence, the gas flows into the liquid collecting section, whereby the state of the liquid collecting section is suppressed from changing to the excessive negative pressure state.

In the storage container described in Japanese Unexamined Patent Publication No. H07-213599, the inside of the liquid collecting section (the storage space) communicates with the outside air while the positive-pressure relief valve is open and while the one-way valve is open. Therefore, infection may occur between the patient and other people. Specifically, while the positive-pressure relief valve is open, the gas in the storage space, that is, the gas in the body cavity of the patient is discharged to the outside, and therefore, if a pathogen is included in the gas, infection to people other than the patient may occur. On the other hand, while the one-way valve is open, the outside air directly flows into the storage space through the one-way valve without passing through the sterile water in the water sealing section, and therefore, if a pathogen is included in the outside air, infection to the patient may occur.

SUMMARY OF INVENTION

It is an object of the present invention to provide a storage container capable of suppressing both the occurrence of infection between a patient and other people and the occurrence of an excessive positive pressure state and an excessive negative pressure state of a storage space.

A storage container according to one aspect of the present invention includes: a storing section including a storage space capable of storing liquid and including an inflow port for causing the liquid to flow into the storage space; and a water sealing section including a coupling space linked to the storage space and a suction space linked to a suction source, the water sealing section being capable of sealing the coupling space and the suction space off from each other with water. The storing section includes an inflow section connectable to a tube to allow the inflow port and an inner side of the tube to communicate and a volume changing section capable of changing the volume of the storage space. The volume changing section is deformed to increase the volume of the storage space when the pressure in the storage space is about to rise to be equal to or higher than a reference pressure set in advance and is deformed to reduce the volume of the storage space when the pressure in the storage space is about to drop to be lower than the reference pressure.

DESCRIPTION OF EMBODIMENTS

A suction device 1 according to an embodiment of the present invention is explained with reference to FIG. 1 to FIG. 11. Note that a posture during use of the suction device 1 is not limited to a posture shown in FIG. 1 to FIG. 4. However, in the following explanation, an up-down direction is defined on the basis of FIG. 1 to FIG. 4 for convenience.

Figure 1:
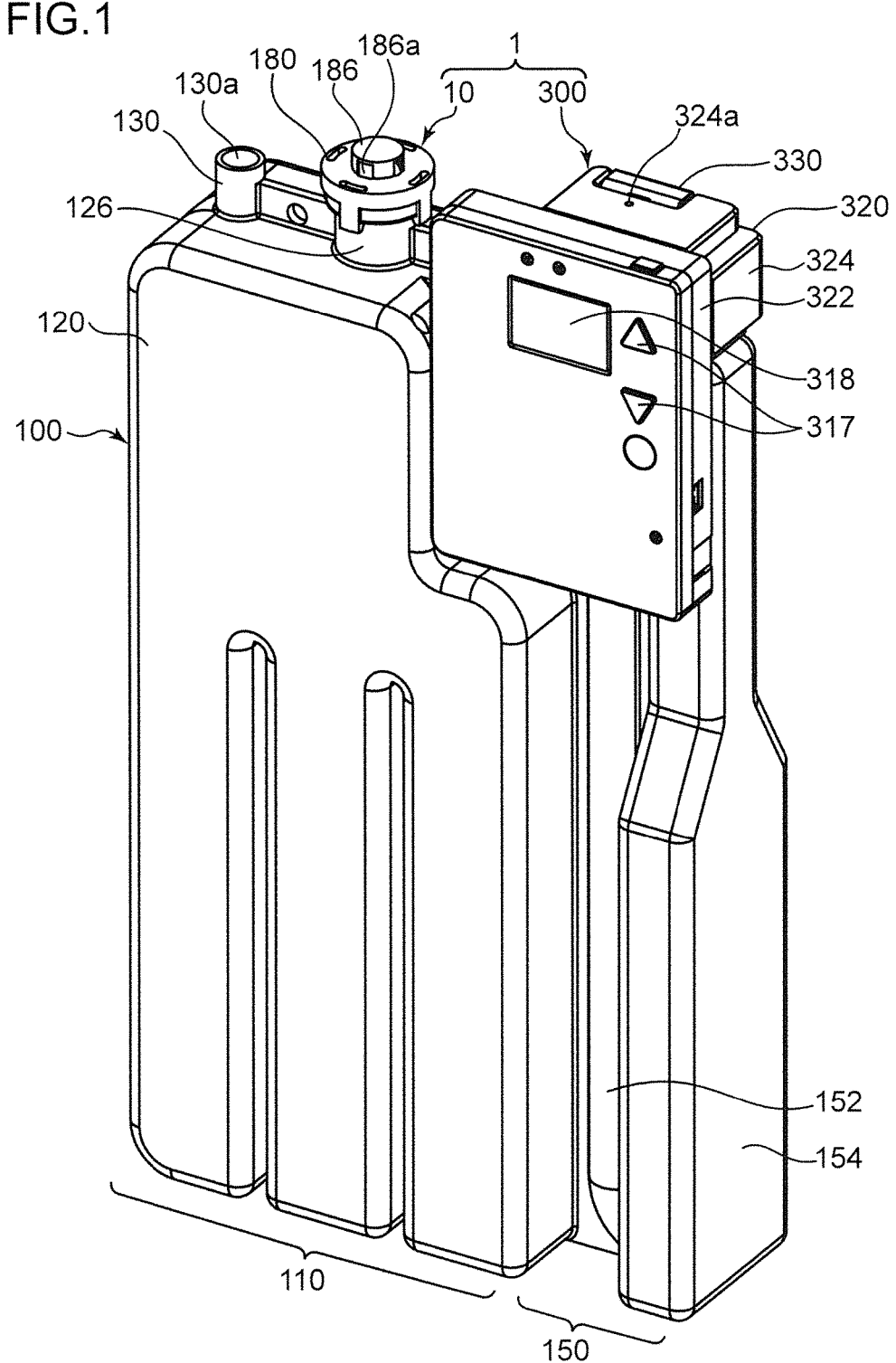
FIG. 1 is a perspective view of a suction device according to an embodiment of the present invention.
Figure 2:
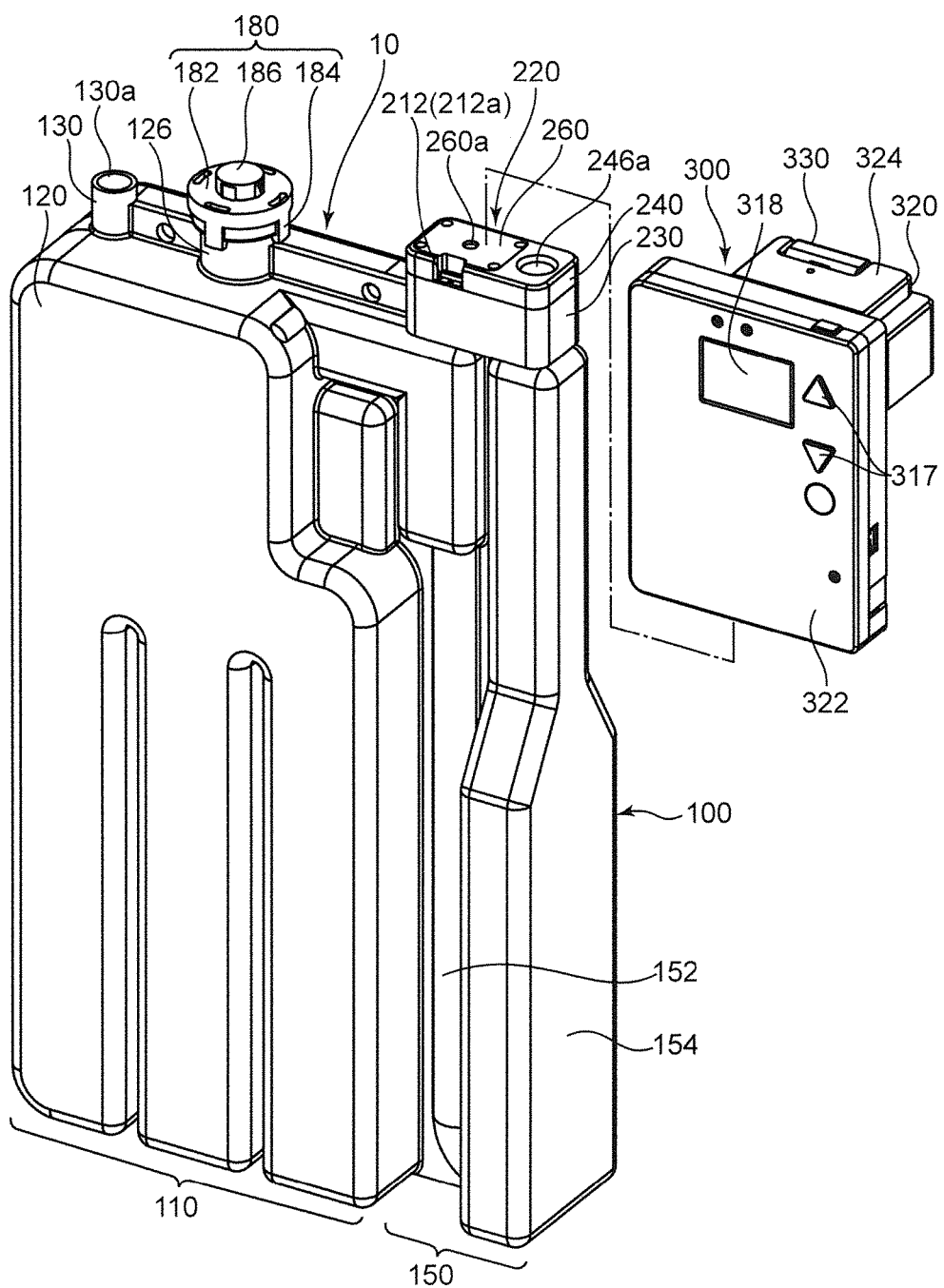
FIG. 2 is a perspective view of a state in which a suction instrument and a control unit of the suction device shown in FIG. 1 have been separated from each other.

As shown in FIG. 1 and FIG. 2, the suction device 1 includes a suction instrument 10 and a control unit 300 capable of being detachably attached to the suction instrument 10.

The suction instrument 10 includes a storage container 100 provided halfway in a suction line for sucking gas and liquid in the body cavity of a patient, a suction pump 210 (see FIG. 3) capable of sucking the gas, and a connecting member 220 for connecting the suction pump 210 to the storage container 100.

The storage container 100 includes a storing section 110 that stores liquid such as body fluid of the patient and a water sealing section 150.

Figure 3:
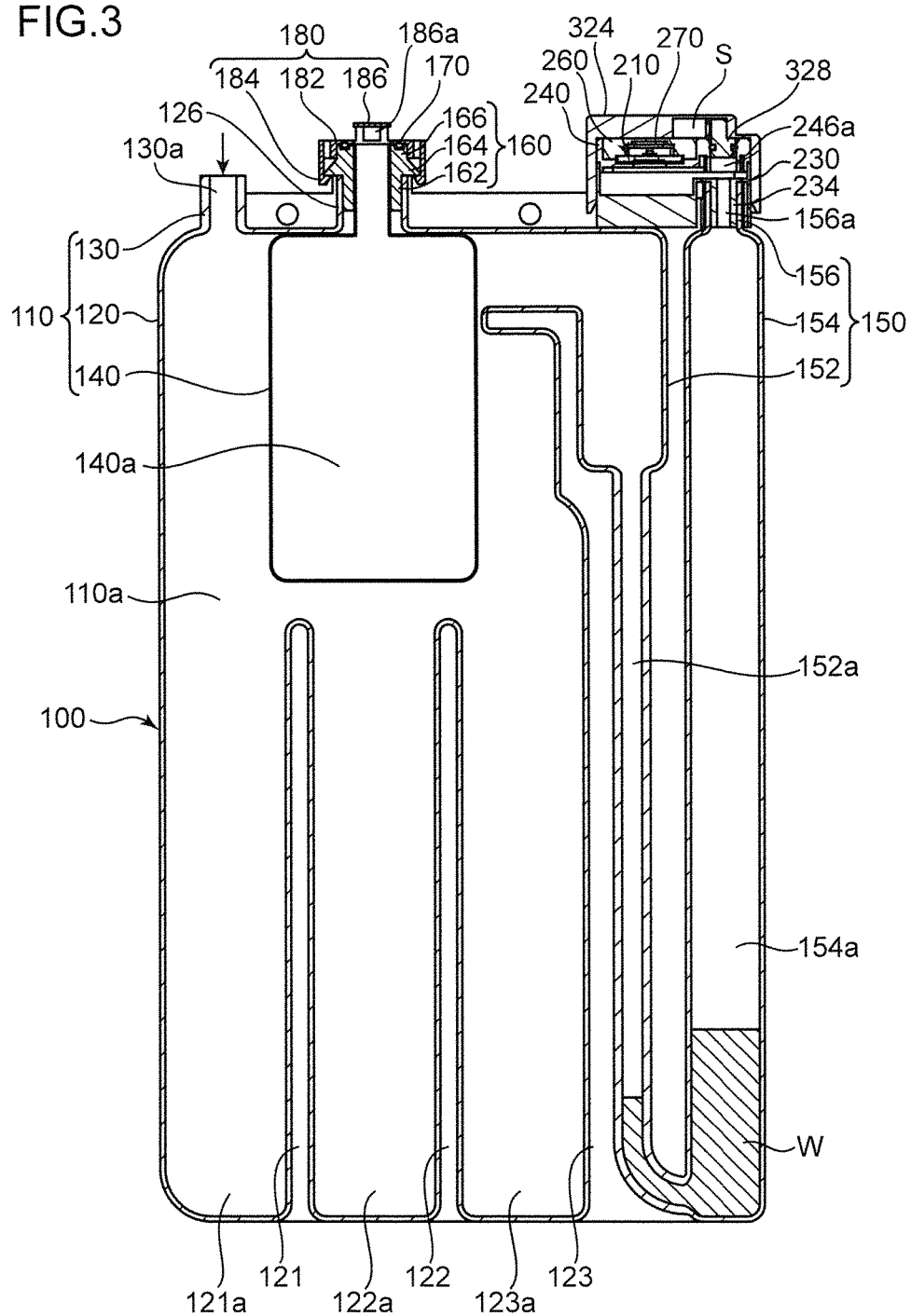
FIG. 3 is a sectional view of the suction device shown in FIG. 1.
Figure 4:
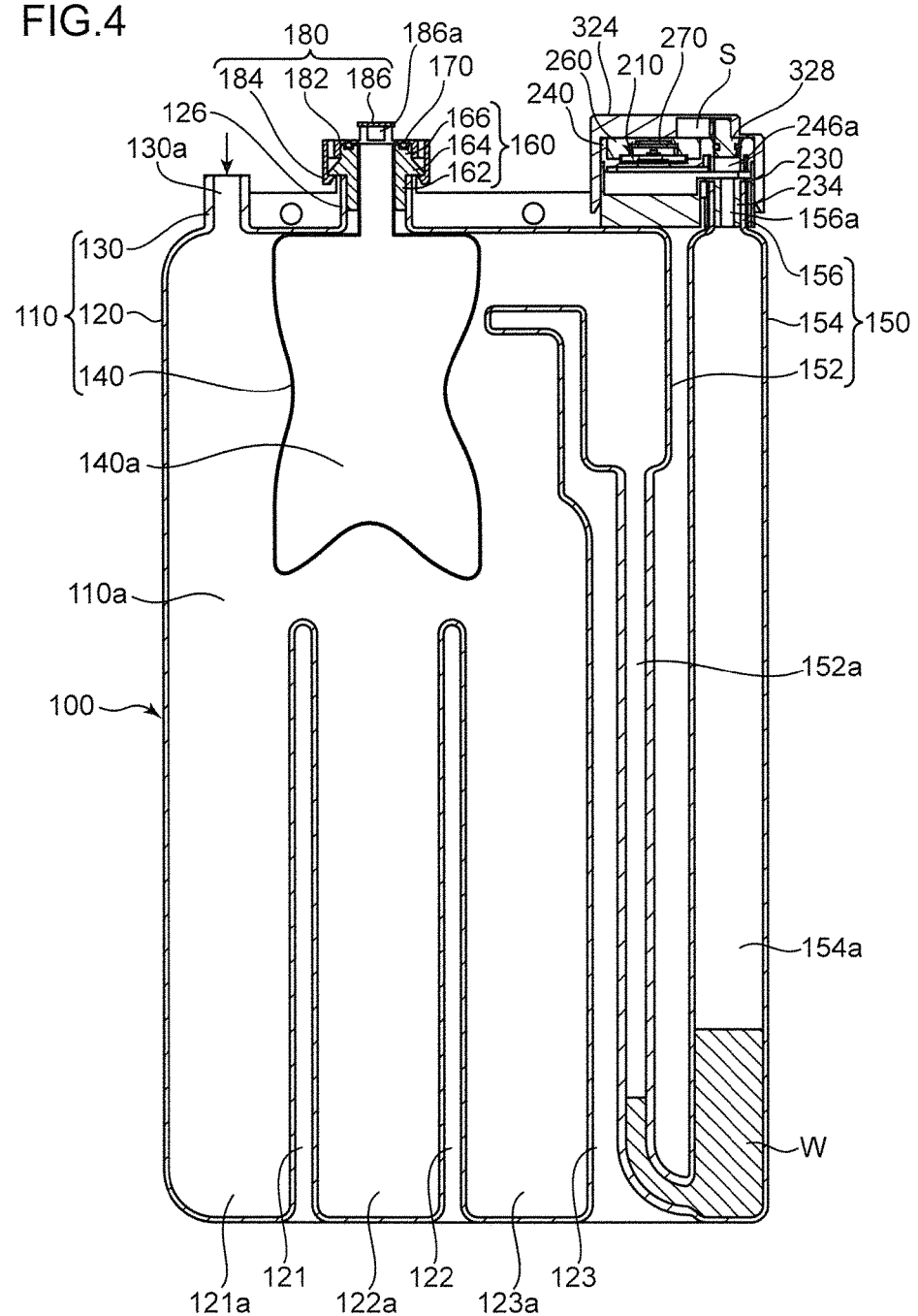
FIG. 4 is a sectional view showing a state in which a volume changing section of the suction device shown in FIG. 1 has been deformed.
Figure 5:
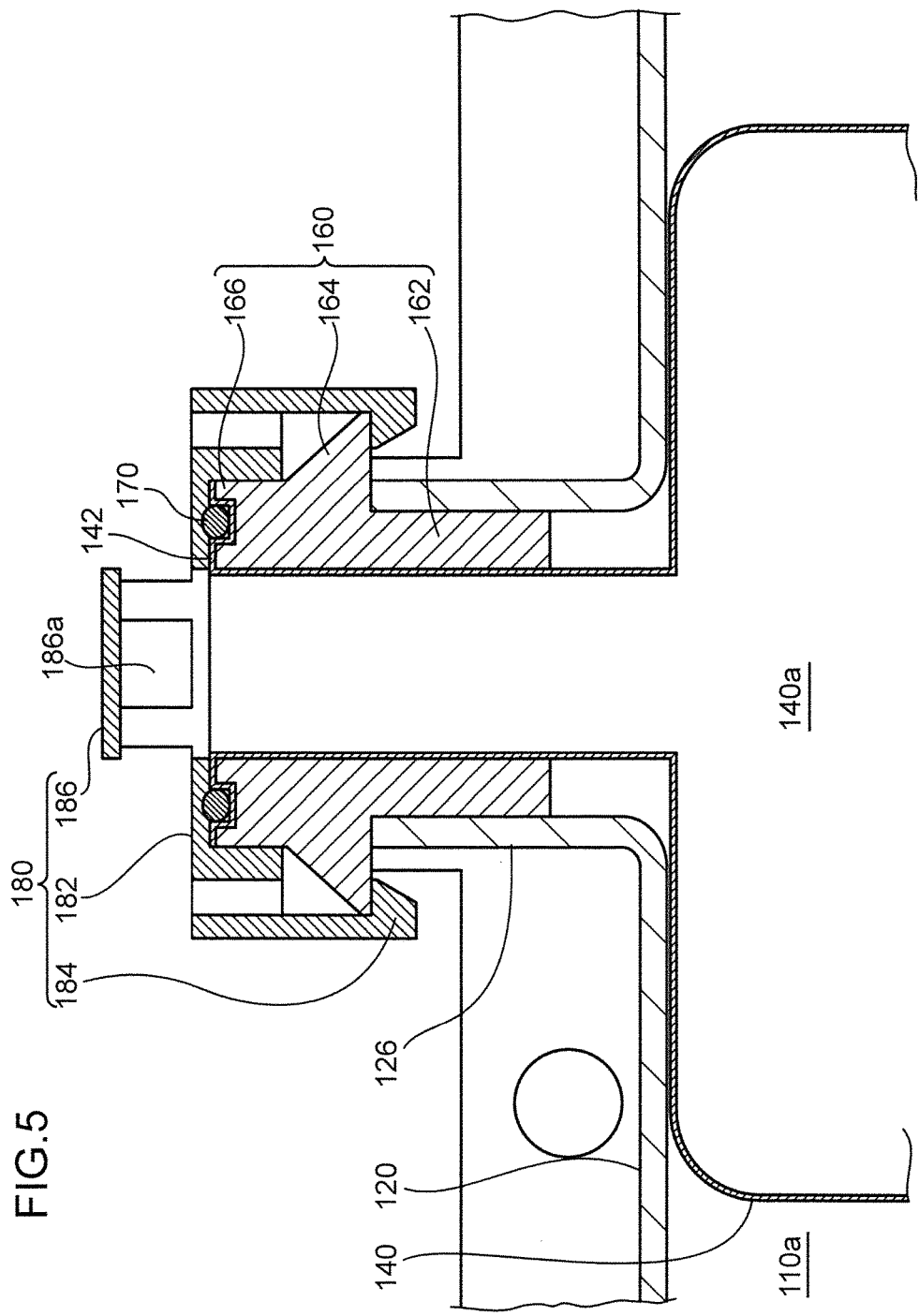
FIG. 5 is an enlarged sectional view of a connecting portion of a storing section main body and the volume hanging section.

The storing section 110 includes a storage space 110a capable of storing the liquid that has flowed out from the body cavity of the patient. The storing section 110 is configured to be capable of changing the volume of the storage space 110a. Specifically, as shown in FIG. 3 and FIG. 4, the storing section 110 includes a storing section main body 120, an inflow section 130, and a volume changing section 140.

The storing section main body 120 assumes a container shape having a substantially rectangular parallelepiped external shape. The storing section main body 120 has rigidity capable of maintaining the external shape of the storing section main body 120 under the atmospheric pressure (enough for preventing the storing section main body 120 from being deformed). The storing section main body 120 includes a first partition wall 121, a second partition wall 122 provided in a position apart from the first partition wall 121 in the right direction, and a third partition wall 123 provided in a position apart from the second partition wall 122 in the right direction. The partition walls 121 to 123 have a shape extending upward from a bottom section of the storing section main body 120. A first storage chamber 121a is formed between the first partition wall 121 and a sidewall of the storing section main body 120. A second storage chamber 122a is formed between the first partition wall 121 and the second partition wall 122. A third storage chamber 123a is formed between the second partition wall 122 and the third partition wall 123.

The inflow section 130 is connected to an upper part of the storing section main body 120. The inflow section 130 is formed in a cylindrical shape surrounding an inflow port 130a for causing the liquid to flow into the storage space 110a. One end of a tube such as a catheter is connected to the inflow section 130 to allow the inflow port 130a and the inner side of the tube to communicate. Note that the other end of the tube is inserted into the body cavity of the patient.

The volume changing section 140 has rigidity lower than the rigidity of the storing section main body 120 and has a shape such as to define the storage space 110a in conjunction with the storing section main body 120. The volume changing section 140 is deformed to increase the volume of the storage space 110a (to suppress the pressure in the storage space 110a from rising to be equal to or higher than a reference pressure set in advance) when the pressure in the storage space 110a is about to rise to be equal to or higher than the reference pressure and is deformed to reduce the volume of the storage space 110a (to suppress the pressure in the storage space 110a from decreasing to be lower than the reference pressure) when the pressure in the storage space 110a is about to drop to be lower than the reference pressure.

The volume changing section 140 is connected to the storing section main body 120 to be located on the inner side of the storing section main body 120. Specifically, the volume changing section 140 is provided in a region further on the water sealing section 150 side (the right side in FIG. 1) than a straight line connecting the inflow port 130a and the first storage chamber 121a on the inner side of the storing section main body 120 so as not to hinder the liquid that has flowed into the storing section main body 120 from the inflow port 130a from flowing to the first storage chamber 121a.

In this embodiment, the volume changing section 140 is formed in a shape (a bag shape) surrounding a buffer space 140a opening upward. A cylindrical attachment section 126 is formed in an upper part of the storing section main body 120. An edge portion 142 (see FIG. 5) of the volume changing section 140 is connected to the attachment section 126. Specifically, a space between the volume changing section 140 and the storing section main body 120 is sealed and the volume changing section 140 is connected to the attachment section 126 to allow the external space (the atmosphere) outside the storage container 100 and the buffer space 140a to communicate. That is, in this embodiment, the storage space 110a is defined by the inner surface of the storing section main body 120 and the inner surface (a surface on the opposite side to the surface on a side communicating with the external space) of the volume changing section 140. A space surrounded by the edge portion 142 of the volume changing section 140 on the inner side of the attachment section 126 configures a "through port" for causing the buffer space 140a to communicate with the external space.

Therefore, in this embodiment, the volume changing section 140 contracts (see FIG. 4) to reduce the volume of the buffer space 140a while pushing out the gas in the buffer space 140a to the external space (the atmosphere) when the pressure in the storage space 110a is about to rise to be equal to or higher than the reference pressure and expands (see FIG. 3) to increase the volume of the buffer space 140a while taking gas into the buffer space 140a from the external space (the atmosphere) when the pressure in the storage space 110a is about to drop to be lower than the reference pressure. In this embodiment, the volume changing section 140 has a shape such as to be accommodated on the inner side of the storing section main body 120 when the pressure in the storage space 110a is equal to or lower than the reference pressure (FIG. 3) and also when the pressure in the storage space 110a exceeds the reference pressure (FIG. 4). The volume changing section 140 has rigidity for maintaining a shape for when the pressure in the storage space 110a is equal to the reference pressure (a shape shown in FIG. 3), when the pressure in the storage space 110a is lower than the reference pressure. In this embodiment, the volume changing section 140 is formed of polyethylene. Note t-hat the volume of the buffer space 140a is set to be larger than the volume of gas that temporarily flows into the storing section 110 through the inflow port 130a when the patient coughs or sneezes.

Figure 10:
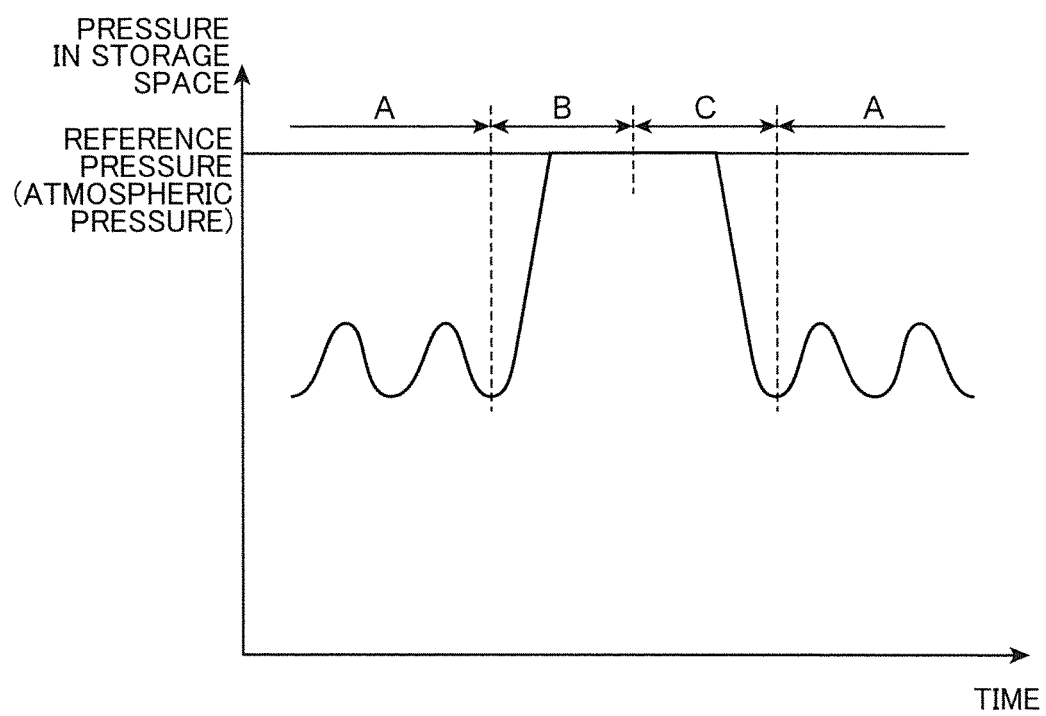
FIG. 10 is a diagram showing a transition of the pressure in a storage space.

As shown in FIG. 10, the reference pressure is set to a value higher than a range of pressure fluctuation of the storage space 110a involved in breathing in a steady state A of the patient and smaller than pressure generated in the storage space 110a (hereinafter referred to as "instantaneous pressure") when a large amount of gas equal to or larger than an amount of gas in the steady state A temporarily flows into the storing section 110 because, for example, the patient coughs and when the volume changing section 140 is not deformed. Note that, in the steady state A, gas in the storage container 100 is sucked by the suction pump 210, and therefore the pressure in the storage space 110a in the steady state A is negative pressure with respect to the pressure in the external space (the atmospheric pressure). The instantaneous pressure is larger than the atmospheric pressure. In this embodiment, since the buffer space 140a communicates with the atmosphere, the reference pressure is set to the atmospheric pressure.

In this embodiment, the volume changing section 140 is connected to the attachment section 126 by an inner plug 160, an O-ring 170, and a lid section 180.

The inner plug 160 includes a cylinder section 162 press-fit into the attachment section 126, a projecting section 164 projecting outward from the cylinder section 162, and a placing section 166 on which the O-ring 170 is placed. The cylinder section 162 is press-fit into the attachment section 126, whereby a space between the cylinder section 162 and the attachment section 126 is sealed and the rear surface of the projecting section 164 comes into contact with the upper end of the attachment section 126. The placing section 166 is connected to upper parts of the cylinder section 162 and the projecting section 164.

The lid section 180 includes a pressing section 182 that presses the O-ring 170, an engaging section 184 that engages with the projecting section 164, and a shielding section 186. The pressing section 182 is formed in a flat shape having an outer diameter slightly larger than the inner plug 160. A hole piercing through the pressing section 182 in the up-down direction is formed in the center of the pressing section 182. The engaging section 184 has a shape extending downward from the outer circumferential edge of the pressing section 182. The engaging section 184 engages with the projecting section 164, whereby the O-ring 170 is held between the rear surface of the pressing section 182 and the upper surface of the placing section 166. Consequently, the space between the volume changing section 140 and the storing section main body 120 is sealed. The shield section 186 has a shape orthogonal to the axial direction of the attachment section 126. The shield section 186 is formed in a position separated upward from the pressing section 182 such that an opening 186a that allows circulation of the gas between the external space and the buffer space 140a in the volume changing section 140 is formed between the shield section 186 and the pressing section 182. Note that the opening 186a is set to a size for allowing circulation of the gas between the external space and the buffer space 140a in the volume changing section 140 and, on the other hand, inhibiting insertion of a finger.

The water sealing section 150 includes a communication section 152 including a communication space 152a, a suction section 154 including a suction space 154a, and an outflow section 156 including an outflow port 156a.

The communication section 152 has a shape such as to define the communication space 152a so that an upper part of the communication space 152a and an upper part of the storage space 110a are linked in the left-right direction. Specifically, the communication section 152 assumes a tubular shape extending in the up-down direction.

The suction section 154 has a shape such as to define the suction space 154a so that a lower part of the suction space 154a and a lower part of the communication space 152a are linked in the left-right direction. Specifically, the suction section 154 assumes a tubular shape extending in the up-down direction.

The outflow section 156 is connected to an upper part of the suction section 154. The outflow section 156 is formed in a tubular shape surrounding an outflow port 156a for causing gas in the suction space 154a to the outside of the storage container 100. In this embodiment, the outflow section 156 is connected to the upper part of the suction section 154 in a posture in which the center axis of the outflow section 156 is parallel to the up-down direction.

Sterile distilled water W (water sealing liquid) of an amount for blocking the link of the communication space 152a and the suction space 154a is injected into the water sealing section 150 through the outflow port 156a, whereby the communication space 152a with storage space 110a, and the suction space 154a are sealed off from each other by water.

Figure 6:
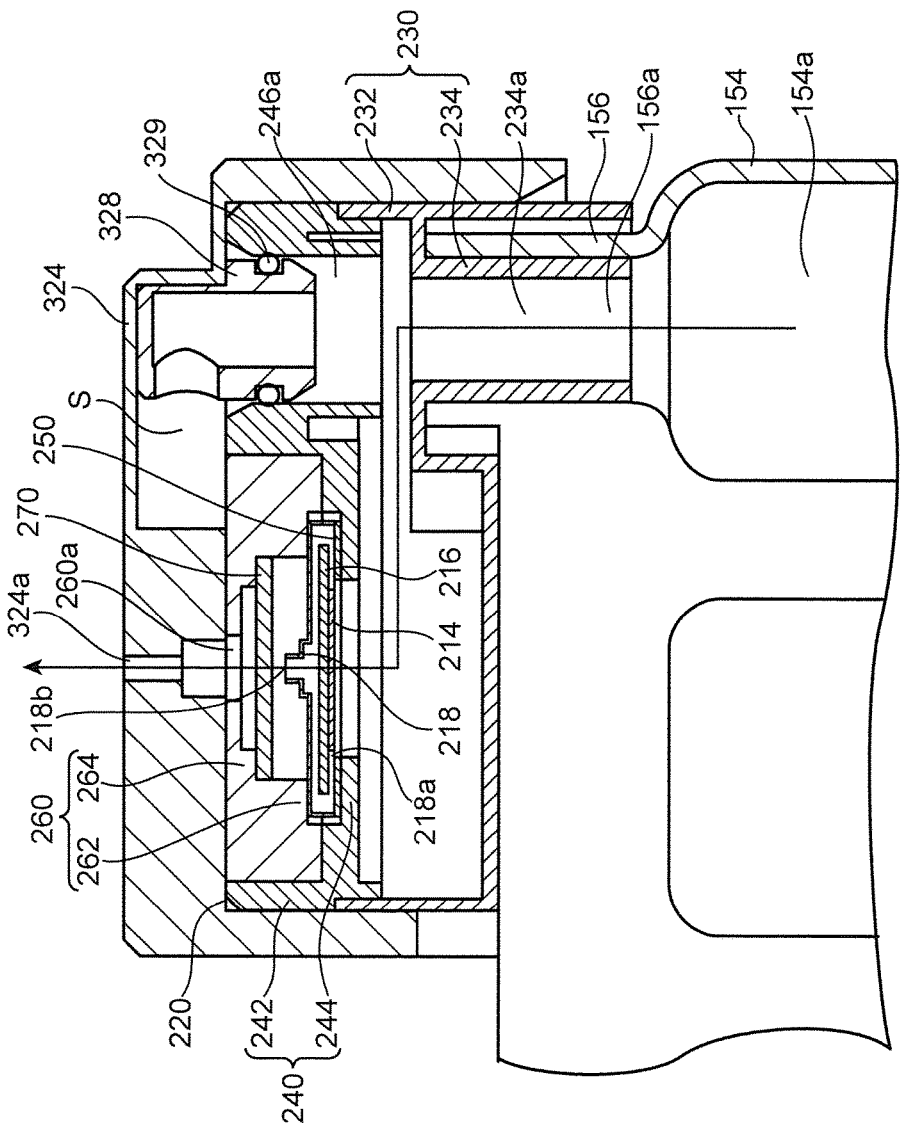
FIG. 6 is an enlarged sectional view of the vicinity of a connecting member.
Figure 7:
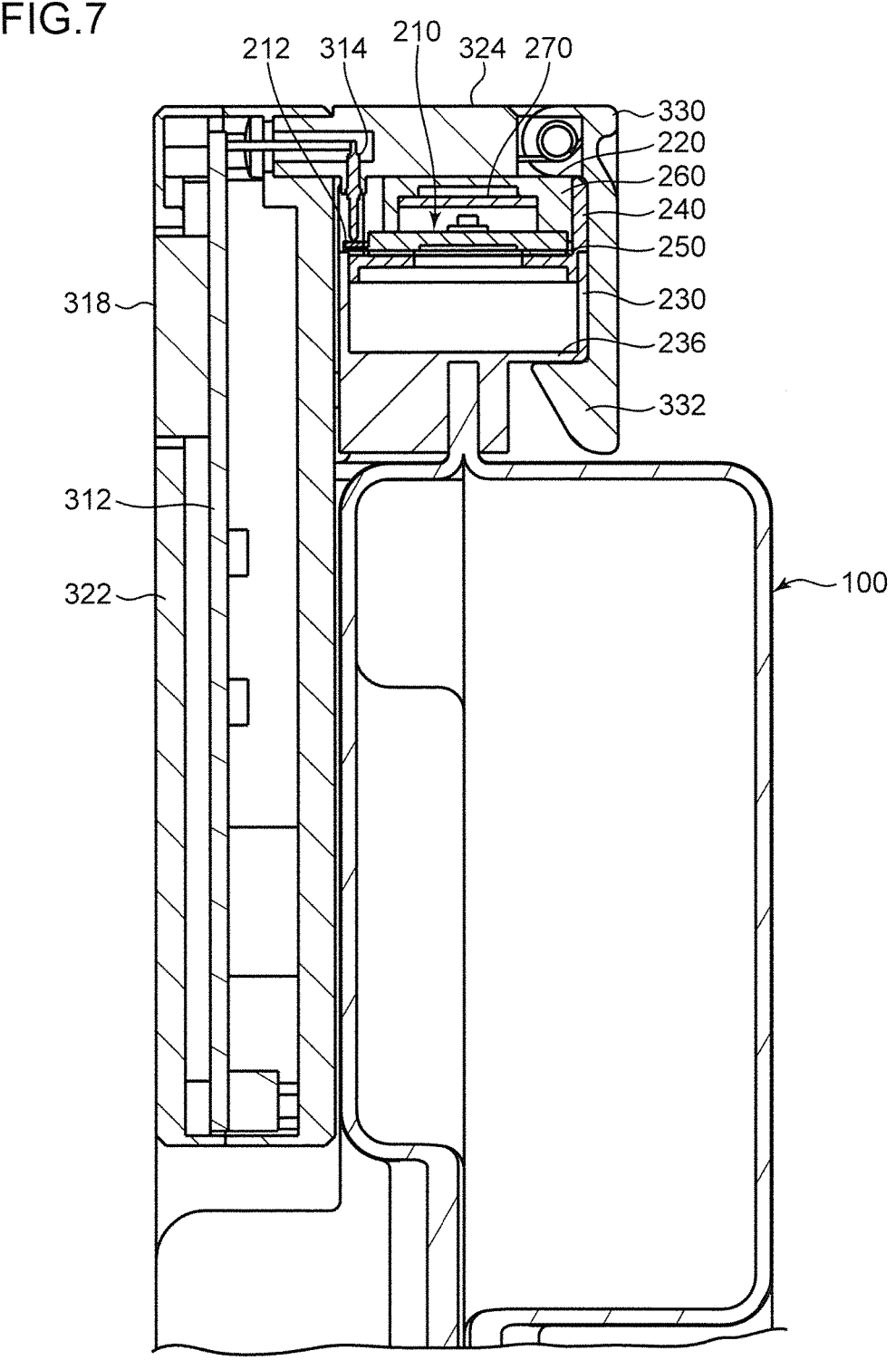
FIG. 7 is a sectional view showing the vicinity of a suction pump.

As shown in FIG. 2, FIG. 6, and FIG. 7, the suction pump 210 includes a connection conductor 212 connectable to the control unit 300, a piezoelectric element 214 connected to the connection conductor 212, a diaphragm 216 connected to the piezoelectric element 214, and a casing 218. That is, the suction pump 210 in this embodiment is a so-called diaphragm pump.

The proximal end portion of the connection conductor 212 is connected to the piezoelectric element 214. The distal end portion of the connection conductor 212 includes a flat upper surface 212a. The upper surface 212a of the distal end portion is connected to the control unit 300.

The piezoelectric element 214 repeats expansion and contraction with a driving voltage supplied from the control unit 300 via the connection conductor 212.

The diaphragm 216 vibrates according to the expansion and the contraction of the piezoelectric element 214.

The casing 218 holds the connection conductor 212, the piezoelectric element 214, and the diaphragm 216. Specifically, the casing 218 holds the piezoelectric element 214 and the diaphragm 216 to surround the piezoelectric element 214 and the diaphragm 216 and holds the connection conductor 212 such that the distal end portion of the connection conductor 212 is exposed. An air intake port 218a for sucking gas is formed in a bottom section of the casing 218.

A discharge port 218b is formed in an upper part of the casing 218 in order to discharge the gas. The diaphragm 216 vibrates, whereby the gas that has flowed into the casing 218 from the air intake port 218a is discharged from the discharge port 218b.

The connecting member 220 is a member for connecting the suction pump 210 to the storage container 100 such that the gas in the storage container 100 is capable of being sucked by the suction pump 210 through the outflow port 156a and the sterile distilled water W is capable of being injected to the water sealing section 150 through the outflow port 156a. Specifically, the connecting member 220 includes a connector 230 connected to the storage container 100, a base 240 joined to the connector 230, a cover 260 joined to the base 240, and a filter 270 capable of capturing pathogens and the like.

The connector 230 includes a section to be connected 234 connected to the outflow section 156 and a peripheral wall 232 connected to the section to be connected 234. The section to be connected 234 has a shape capable of being press-fit into the outflow section 156 of the storage container 100. Specifically, the section to be connected 234 is formed in a cylindrical shape having an outer diameter slightly smaller than the inner diameter of the outflow section 156 and surrounding a connection port 234a. The peripheral wall 232 has a shape for widening the connection port 234a. Specifically, the peripheral wall 232 assumes a square cylindrical shape surrounding the peripheral wall 232 on the outer side of the section to be connected 234. As shown in FIG. 7, in the peripheral wall 232, a mounting section 236 to which the control unit 300 is detachably mountable is formed.

The base 240 includes a supporting section 244 that supports the suction pump 210, an injection port 246a for enabling injection of the sterile distilled water W (the water sealing liquid) into the connecting member 220, and a joining wall 242. In this embodiment, the suction pump 210 is supported by the supporting section 244 via an elastic sheet 250 that seals a space between the suction pump 210 and the supporting section 244. The injection port 246a has a shape piercing through the base 240 in the up-down direction. The joining wall 242 is formed in a square cylindrical shape surrounding the supporting section 244 and the inject port 246a and capable of being joined to the upper end portion of the peripheral wall 232 of the connector 230. In a state in which the joining wall 242 has been joined to the peripheral wall 232, the supporting section 244 is disposed in a position shifted in the left-right direction with respect to the connection port 234a and the injection port 246a is disposed in a position overlapping the connection port 234a in the up-down direction. The joining wall 242 is jointed to the peripheral wall 232 and the section to be connected 234 is connected to the outflow section 156, whereby an exhaust channel leading from the outflow port 156a to the suction pump 210 is formed. Consequently, it is possible to suck the gas in the suction space 154a with the suction pump 210 and inject the sterile distilled water W into the water sealing section 150 through the injection port 246a and the outflow port 156a.

The cover 260 is joined to the base 240 to cover the suction pump 210. Specifically, the cover 260 is press-fit into a region on the supporting section 244 and on the inner side of the joining wall 242 in the base 240. The cover 260 includes a discharge port 260a for discharging, to the outside, the gas discharged from the suction pump 210. In this embodiment, the cover 260 includes a pressing section 262 that presses the suction pump 210 against the supporting section 244 and a filter holding section 264 that holds the filter 270. In a state in which the cover 260 is joined to the base 240, the pressing section 262 holds the suction pump 210 from both sides in the up-down direction in conjunction with the supporting section 244. The filter holding section 264 is formed between the pressing section 262 and the discharge port 260a, that is, on a downstream side of the suction pump 210. The filter holding section 264 holds a peripheral edge portion of the filter 270. The area of the filter 270 in a state in which the filter holding section 264 holds the filter 270 is set larger than the opening area of the discharge port 218b. Therefore, the gas discharged from the discharge port 218b spreads to a space between the filter holding section 264 and the pressing section 262, that is, a space between the filter 270 and the upper surface of the casing 218 and thereafter passes through the filter 270 while coming into contact with the entire surface of the filter 270. Note that the filter 270 is attached to the filter holding section 264 by bonding or the like.

The control unit 300 is a unit that is detachably attachable to the suction instrument 10 and mainly controls driving of the suction pump 210. Specifically, the control unit 300 includes a control board 310 and a holding member 320 that holds the control board 310 and is capable of being attached to and detached from the suction instrument 10.

Figure 8:
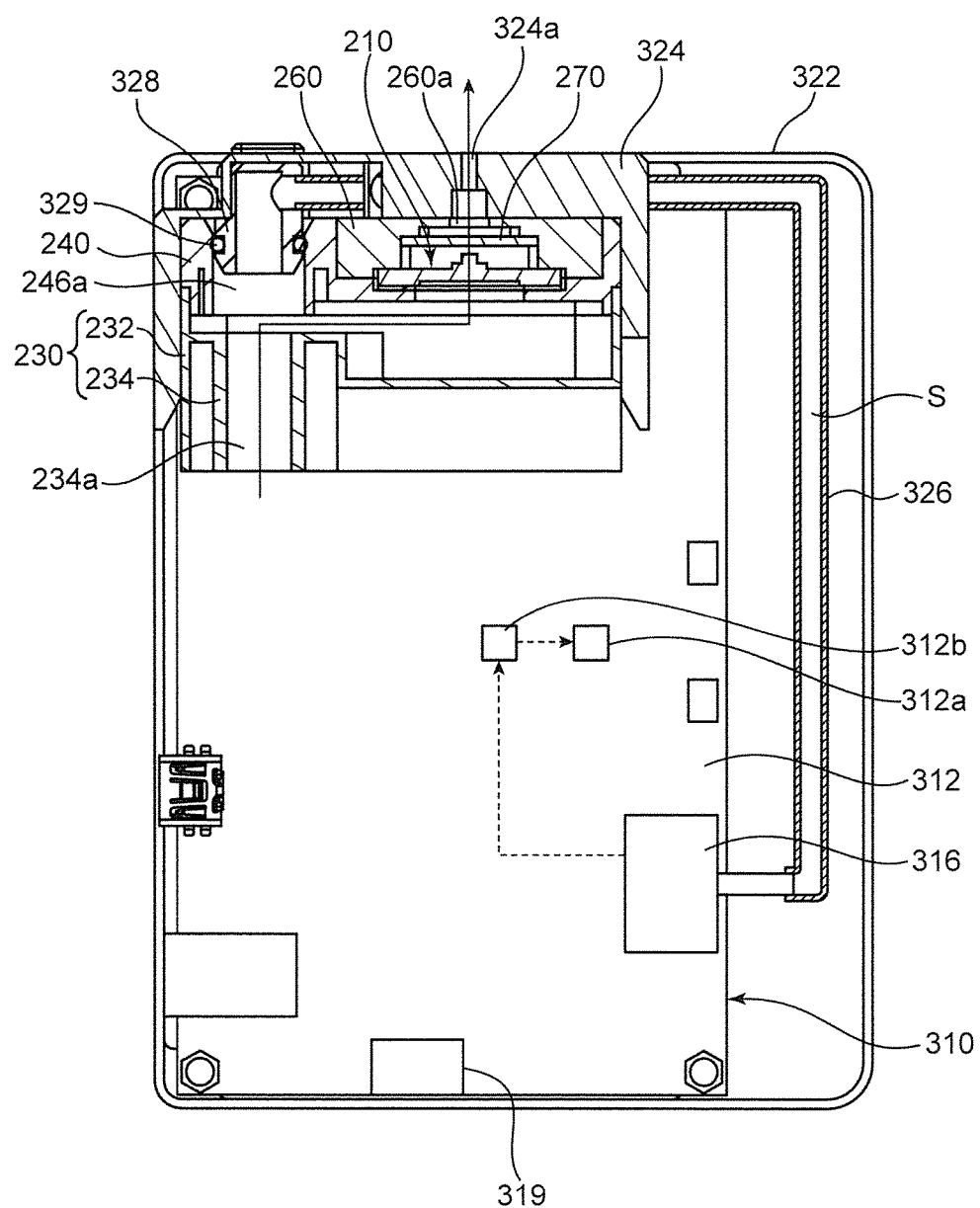
FIG. 8 is a sectional view along a surface passing a connection terminal and a section to be mounted.
Figure 9:
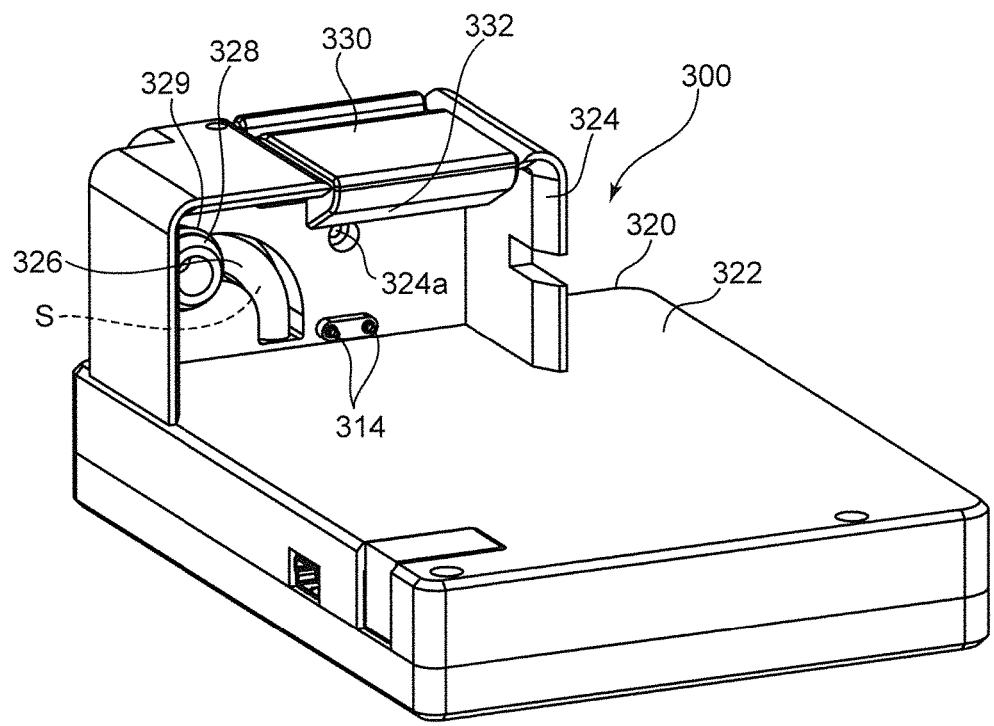
FIG. 9 is a perspective view of the control unit.

As shown in FIG. 8 and FIG. 9, the control board 310 includes a substrate 312 on which a printed circuit is formed, connection terminals 314 connected to the substrate 312, and a pressure sensor 316 mounted on the substrate 312.

The printed circuit formed on the substrate 312 includes a voltage supplying section 312a that supplies the driving voltage to the piezoelectric element 214.

The connection terminals 314 have a shape such as to be connectable to the connection conductor 212 of the suction pump 210. Specifically, the connection terminals 314 have a shape extending downward from the upper end portion of the substrate 312 to come into contact with the upper surface 212a of the distal end portion of the connection conductor 212 from above. The lower ends of the connection terminals 314 and the upper surface 212a of the distal end portion of the connection conductor 212 come into contact with each other, whereby the printed circuit and the piezoelectric element 214 conduct.

In this embodiment, an operation switch 317 (FIG. 1), a display element 318 (FIG. 1), a battery 319 (FIG. 8), and the like are further mounted on the substrate 312. The operation switch 317 is an element for setting a suction pressure. The display element 318 is an element that displays the suction pressure and the like. The battery 319 is an element that supplies electric power to the printed circuit formed on the substrate 312 and the element mounted on the substrate 312.

The holding member 320 includes a holding member main body 322 that holds the substrate 312, a projecting wall 324 projecting from the holding member main body 322, a defining section 326, a coupling section 328, and a section to be mounted 330 detachably mountable on the suction instrument 10.

The holding member main body 322 holds the substrate 312 in a posture in which the lower ends of the connection terminals 314 are exposed.

The projecting wall 324 has a shape projecting toward the opposite side (the right side in FIG. 7) from a side where the display element 318 is mounted in a direction parallel to the thickness direction of the substrate 312 from an upper part of the holding member main body 322. The projecting wall 324 includes an exhaust port 324a for discharging, to the outside, the gas discharged from the suction pump 210. The exhaust port 324a communicates with the discharge port 260a of the cover 260.

The defining section 326 defines a detection space S in which pressure is detected by the pressure sensor 316. The defining section 326 may be a tube or the like that surrounds the detection space S.

The coupling section 328 has a shape for coupling the defining section 326 and the base 240 such that the detection space S and the exhaust channel are connected. Specifically, as shown in FIG. 8, the coupling section 328 is formed in a cylindrical shape having a center axis capable of being press-fit into the injection port 246a of the base 240 and extending in a direction parallel to the up-down direction. The coupling section 328 is held by the projecting wall 324. One end of the coupling section 328 is connected to the defining section 326. The other end of the coupling section 328 is press-fit into the injection port 246a. In this embodiment, the coupling section 328 is press-fit into the injection port 246a such that an O-ring 329 is held between the outer circumferential surface of the coupling section 328 and the inner circumferential surface surrounding the injection port 246a. Consequently, a space between the coupling section 328 and the injection port 246a is sealed. Consequently, the injection port 246a is blocked from the external space and the exhaust channel and the detection space S communicate. In this state, the pressure in the detection space S is equal to the pressure in the suction space 154a or the exhaust channel. Therefore, the pressure sensor 316 detects the pressure in the suction space 154a or the exhaust channel, that is, the pressure in the body cavity of the patient. Note that a difference equivalent to pressure by the sterile distilled water W in the water sealing section 150 is present between the pressure in the suction space 154a or the exhaust channel and the pressure in the body cavity of the patient (the pressure in the storage space 110a). In the following explanation, however, it is assumed that the pressures are equal. Since the pressure in the detection space S and the pressure in the exhaust channel are equal, the gas that has flowed out from the suction space 154a flows along the exhaust channel without flowing into the detection space S and is discharged to the outside from the exhaust port 324a through the suction pump 210 and the filter 270.

The printed circuit further includes a voltage control section 312b. The voltage control section 312b controls a value of the driving voltage supplied by the voltage supply section 312a to set a detection value of the pressure sensor 316 to a suction pressure set in advance by operation of the operation switch 317. That is, the value of the driving voltage is subjected to feedback control on the basis of the detection value of the pressure sensor 316.

The section to be mounted 330 has a shape capable of being detachably mounted on the connector 230 of the suction instrument 10. The section to be mounted 330 has a shape extending downward from an end portion on the opposite side of a side connected to the holding member main body 322 in the projecting wall 324. Specifically, the section to be mounted 330 has a shape mountable on the mounting section 236 in an attached state (a state in which the lower ends of the connection terminals 314 are in contact with the upper surface 212a of the distal end portion of the connection conductor 212 and the coupling section 328 is coupled to the injection port 246a). In this embodiment, as shown in FIG. 7 and FIG. 8, the section to be mounted 330 includes an engaging section 332 that engages with the mounting section 236 in the mounted state. The section to be mounted 330 is displaceable between an engaged posture in which the engaging section 332 engages with the mounting section 236 in the mounted state and a disengaged posture in which the engaging section 332 disengages from the mounting section 236 in the mounted state.

A manufacturing method for the suction device 1 is explained.

First, the suction pump 210 is fixed to the connecting member 220. Specifically, the base 240 is joined to the connector 230. The suction pump 210 is supported by the supporting section 244 of the base 240 via the elastic sheet 250. The cover 260 is joined to the base 240 in a state in which the filter 270 is held by the filter holding section 264 of the cover 260.

The connecting member 220 is connected to the outflow section 156 of the storage container 100. Specifically, the section to be connected 234 of the connector 230 is press-fit into the outflow section 156.

Subsequently, a method of using the suction device 1 is explained.

First, the sterile distilled water W (the water sealing liquid) is injected into the water sealing section 150 through the injection port 246a of the base 240, the connection port 234a of the connector 230, and the outflow port 156a, such that the communication space 152a with storage space 110a, and the suction space 154a are sealed off from each other by water.

Thereafter, the control unit 300 is attached to the suction instrument 10. Specifically, the control unit 300 is brought close to the suction instrument 10 from above such that the lower ends of the connection terminals 314 come into contact with the upper surface 212a of the distal end portion of the connection conductor 212 and the coupling section 328 is press-fit into the injection port 246a. In a state (a mounted state) in which the lower ends of the connection terminals 314 are in contact with the upper surface 212a of the distal end portion of the connection conductor 212 and the coupling section 328 is press-fit into the injection port 246a, the section to be mounted 330 is set in the engaged posture such that the section to be mounted 330 is mounted on the mounting section 236. Consequently, the suction pump 210 becomes capable of being driven. Further, during the driving of the suction pump 210 (during suction treatment), the voltage control section 312b becomes capable of controlling the driving voltage of the voltage control section 312b such that the pressure in the detection space S (the pressure in the body cavity of the patient) reaches a desired suction pressure.

Subsequently, one end of a tube such as a catheter is connected to the inflow port 130a and the tube is closed by a clamp or the like. Consequently, the storage space 110a is blocked from the external space (the outdoor air). A desired suction pressure is set by the operation of the operation switch 317. Note that the suction pressure is a value lower than the reference pressure (in this embodiment, the atmospheric pressure).

The driving voltage is supplied from the voltage supplying section 312a to the suction pump 210 in this state. Then, the suction pump 210 is driven and the pressure in the storage space 110a approaches a suction pressure equal to or lower than the reference pressure. In this state, the other end of the tube is inserted into the body cavity (the thoracic cavity) of the patient and the clamp is removed. Then, liquid and gas in the body cavity of the patient flows into the storing section main body 120 through the inflow port 130a and the pressure in the body cavity of the patient is equalized with the pressure in the storage space 110a. The liquid that has flowed into the storage section main body 120 is stored in the bottom section (the first storage chamber 121*a* to the third storage chamber 123*a*) of the storing section main body 120. On the other hand, the gas that has flowed into the storing section main body 120 changes to air bubbles and passes through the sterile distilled water W of the water sealing section 150 and thereafter passes through the suction space 154*a* and the outflow port 156*a* and is discharged to the outside from the exhaust port 324*a* through the exhaust channel, that is, through the suction pump 210 and the filter 270.

Figure 11:
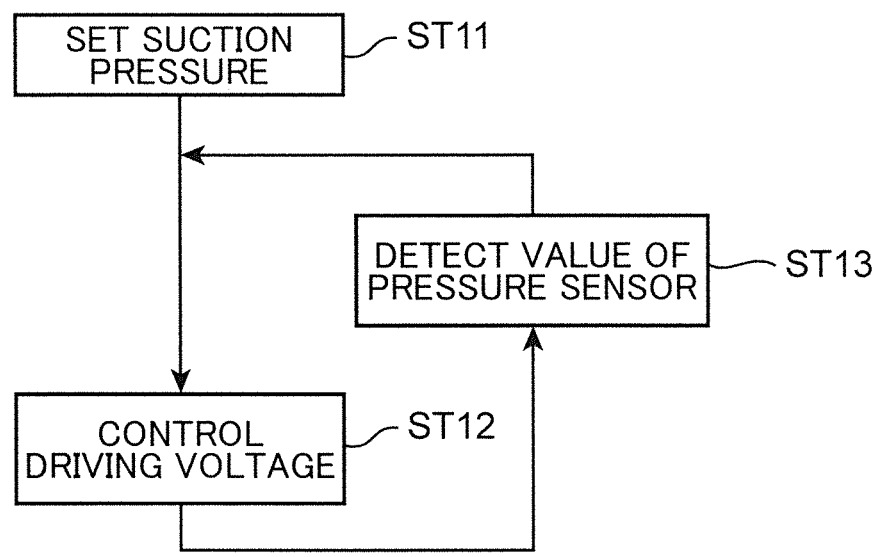
FIG. 11 is a flowchart showing control details of the control unit.

During the driving of the suction pump 210 (during the suction treatment), the voltage control section 312*b* controls the driving voltage, whereby the pressure in the detection space S (the suction space 154*a*), that is, the pressure in the body cavity of the patient is controlled to be the suction pressure set in advance. Specifically, as shown in FIG. 11, when the suction pressure is set by the operation of the operation switch 317 (step ST11), the voltage control section 312*b* controls (adjusts) the driving voltage supplied to the suction pump 210 by the voltage supplying section 312*a* (step ST12). Thereafter, the pressure sensor 316 detects the pressure in the detection space S (the suction space 154*a*), that is, the pressure in the body cavity of the patient (step ST13). The voltage control section 312*b*, which has received a detection value of the pressure sensor 316, controls (adjusts) the driving voltage supplied to the suction pump 210 by the voltage supplying section 312*a* such that a difference between the detection value and the suction pressure becomes zero (step ST12).

During the suction treatment performed using the suction device 1, when a large amount (an amount larger than an amount involved in the respiration in the steady state A) of gas temporarily flows into the storing section main body 120 from the inflow port 130*a* because, for example, the patient coughs, the pressure in the storage space 110*a* rises (see FIG. 10). In the suction device 1, the state of the storage space 110*a* is suppressed from changing to the excessive positive pressure state according to the pressure rise of the storage space 110*a* at this point and the state of the storage space 110*a* is suppressed from changing to the excessive negative pressure state according to a pressure decrease after that by the deformation of the volume changing section 140. Specifically, when the pressure in the storage space 110*a* is about to rise to be equal to or higher than the reference pressure (in this embodiment, the atmospheric pressure) because, for example, the patient coughs, the volume changing section 140 is deformed to increase the volume of the storage space 110*a* (to suppress the rise in the pressure in the storage space 110*a*), and therefore the state of the storage space 110*a* is suppressed from changing to the excessive positive pressure state. More specifically, as shown in FIG. 10, when the pressure in the storage space 110*a* reaches the reference pressure in a period B in which an amount of gas larger than an amount of gas in the steady state A flows into the storage space 110*a* because, for example, the patient coughs, the volume changing section 140 is deformed (contracts) to push out a volume of gas, which is equivalent to a volume of the gas that flows into the storage space 110*a* thereafter, from the buffer space 140*a* to the external space (the atmosphere) (FIG. 4). Therefore, the pressure in the storage space 110*a* is maintained at the reference pressure. After a large amount of gas temporarily flows into the storage space 110*a* (after the patient coughs, etc.), when the gas flows out from the storage space 110*a* to the outside of the storing section 110 (into the body cavity of the patient) through the inflow port 130*a*, whereby the pressure in the storage space 110*a* is about to drop to be lower than the reference pressure, the volume changing section 140 is deformed to reduce the volume of the storage space 110*a* (suppress a decrease in the pressure in the storage space 110*a*). Therefore, the state of the storage space 110*a* is suppressed from changing to the excessive negative pressure state. More specifically, as shown in FIG. 10, in a period C in which the gas flows out into the body cavity of the patient from the storage space 110*a* through the inflow port 130*a* after a large amount of gas temporarily flows into the storage space 110*a* (after the period B), the volume changing section 140 is deformed (expands) to take a volume of gas, same as the volume of the gas above, into the buffer space 140*a* from the external space (the atmosphere). Therefore, the pressure in the storage space 110*a* is maintained at the reference pressure. That is, while the volume changing section 140 expands, the pressure in the storage space 110*a* does not drop. After the volume changing section 140 fully expands in the period C, that is, after the shape of the volume changing section 140 returns to a shape (FIG. 3) for when the pressure of the volume changing section 140 is equal to or lower than the reference pressure, the pressure in the storage space 110*a* decreases according to the outflow of the gas from the storage space 110*a* into the body cavity. An amount of gas flowing out from the storage space 110*a* into the body cavity of the patient in the period C is substantially the same as the amount of gas that has flowed into the storage space 110*a* from the body cavity of the patient in the period B. Therefore, after the end of the period C, the pressure in the storage space 110*a* (the pressure in the body cavity of the patient) returns to a state substantially the same as a state in the steady state A before the period B. Therefore, the state of the storage space 110*a* is suppressed from changing to the excessive positive pressure state and the excessive negative pressure state.

Moreover, during the use of the storage container 100, the tube is connected to the inflow section 130 and the water sealing section 150 is sealed by water. Therefore, since the storage space 110*a* is blocked from the external space (the atmosphere) of the storing section 110, the occurrence of infection between the patient and other people is suppressed.

That is, in the storage container 100, a part of the storing section 110 including the storage space 110*a* blocked from the external space during the use is the volume changing section 140 capable of changing the volume of the storage space 110*a*. Therefore, both of the occurrence of infection between the patient and other people and the occurrence of the excessive positive pressure state and the excessive negative pressure state of the storage space 110*a* are suppressed.

In this embodiment, the volume changing section 140 has rigidity for maintaining, when the pressure in the storage space 110*a* is equal to or lower than the reference pressure, a shape at a time when the pressure in the storage space 110*a* is equal to the reference pressure. The reference pressure is set to a value smaller than the instantaneous pressure and higher than a range of pressure fluctuation of the storage space 110*a* involved in the respiration in the steady state A of the patient. Therefore, the volume changing section 140 is not deformed by the respiration in the steady state A of the patient. Therefore, for example, the suction of the liquid in the storage container 100 by the suction pump 210 is stopped, whereby a liquid surface of the sterile distilled water W encapsulated in the water sealing section 150 moves up and down according to pressure fluctuation of the storage space 110*a* involved in the respiration during the steady state A of the patient. Therefore, it is possible to check presence or absence of so-called respiratory movement while suppressing the state of the storage space 110a from changing to the excessive positive pressure state and the excessive negative pressure state.

In this embodiment, even in a state where the patient coughs, for example, in addition to the steady state A, the volume changing section 140 is accommodated on the inner side of the storing section main body 120 having rigidity higher than the rigidity of the volume changing section 140, that is, the volume changing section 140 is protected by the storing section main body 120, and therefore damage to the volume changing section 140 is suppressed. Moreover, the occurrence of a deficiency such as a deficiency in which the deformation for increasing the volume of the storage space 110a by the volume changing section 140 is hindered by an obstacle or the like on the outer side of the storing section main body 120 is prevented.

In this embodiment, the volume changing section 140 is in contact with both of the storage space 110a and the external space (the atmosphere). Therefore, the reference pressure is set to any value smaller than the instantaneous pressure and equal to or larger than the pressure in the external space (the atmospheric pressure), whereby the state of the storage space 110a is suppressed from changing to the excessive positive pressure state and the excessive negative pressure state.

The storage container 100 in this embodiment includes the lid section 180 including the shielding section 186 and the opening 186a. Therefore, the deformation of the volume changing section 140 is not hindered and intrusion of foreign substances from the external space into the buffer space 140a in the volume changing section 140 is suppressed.

In the suction device 1, the gas that has flowed into the storage container 100 from the body cavity of the patient through the inflow port 130a is sucked from the outflow port 156a by the suction pump 210 connected to the storage container 100 via the connecting member 220. Therefore, as in the past, a pathogen or the like sucked from the body cavity of the patient is sometimes accumulated in the suction pump 210. However, the suction pump 210 of the suction instrument 10 is the so-called diaphragm pump including the contact conductor 212, the piezoelectric element 214, and the diaphragm 216 and the structure of the suction pump 210 is simple. Therefore, the suction pump 210 is suitable for disposal. Moreover, the suction instrument 10 includes the mounting section 236. The mounting section 236 has a shape on which the control unit 300 that supplies the driving voltage for driving the suction pump 210 (expanding and contracting the piezoelectric element 214) is detachably mountable. Therefore, by the control unit 300 being detached from the suction instrument 10, the suction pump 210, the connecting member 220, and the storage container 100 excluding the control unit 300 can be disposed, and consequently, maintenance work of the suction pump 210 is reduced.

In the suction instrument 10 in this embodiment, a pathogen is captured while an increase in the suction resistance of the suction pump 210 is suppressed. Moreover, the occurrence of clogging of the filter 270 is also suppressed. Specifically, the filter 270 is held by the filter holding section 264 on the downstream side of the suction pump 210, and therefore, compared with when the filter 270 is held on an upstream side of the suction pump 210, an increase in resistance at the time when the suction pump 210 is suppressed. The area of the filter 270 is larger than the area of the discharge port 218b. The filter 270 is held in a position apart from the suction pump 210 to the downstream side. Therefore, the gas discharged from the discharge port 218b passes through the filter 270 while coming into contact with the filter 270 having an area larger than the area of the discharge port 218b. Therefore, the occurrence of clogging of the filter 270 is suppressed.

With the suction instrument 10 in this embodiment, in a state in which the suction pump 210 has been connected to the storage container 100 by the connecting member 220, it is possible to inject the sterile distilled water W (the water sealing liquid) into the water sealing section 150. Specifically, the connecting member 220 includes the injection port 246a formed in a position overlapping the outflow port 156a of the storage container 100 in the up-down direction. Therefore, the injection of the sterile distilled water W (the water sealing water) into the water sealing section 150 through the injection port 246a and the outflow port 156a is allowed. Note that, when the suction treatment for the patient is performed using the suction instrument 10, since the injection port 246a is closed by the control unit 300, it is possible to suck the air in the storage container 100 with the suction pump 210.

Further, the section to be mounted 330 of the control unit 300 in this embodiment has a shape mountable on the mounting section 236 in a state in which the connection terminals 314 are in contact with the connection conductor 212. Therefore, the section to be mounted 330 is mounted on the mounting section 236 of the suction instrument 10, whereby a structure in which the connection terminals 314 and the connection conductor 212 are connected to each other is constructed. Therefore, a wiring cable or the like for connecting the connection conductor 212 and the connection terminals 314 is omitted. After the mounting of the control unit 300 on the suction instrument 10 is completed, the driving voltage is supplied from the voltage supplying unit 312a of the control board 310 to the piezoelectric element 214 via the connection terminals 314 and the connection conductor 212, whereby the gas in the storage container 100 is sucked by the suction pump 210. Further, the section to be mounted 330 is detachably mountable on the mounting section 236. Therefore, after the suction treatment for the patient ends, the section to be mounted 330 is detached from the mounting section 236, whereby it is possible to reuse the control unit 300. On the other hand, the suction instrument 10 (the storage container 100, the suction pump 210, the connecting member 220) is discarded. Therefore, maintenance work for the suction pump 210 of the suction instrument 10 is reduced.

Further, the section to be mounted 330 has a shape mountable on the mounting section 236 in a state in which the coupling section 328 is coupled to the injection port 246a of the connecting member 220. Therefore, the section to be mounted 330 is mounted on the mounting section 236, whereby the connection terminal 314 and the connection conductor 212 are connected to each other. Moreover, the exhaust channel and the detection space S communicate. That is, the section to be mounted 330 is mounted on the mounting section 236, whereby the suction pump 210 becomes capable of being driven. Further, during the driving of the suction pump 210 (during the suction treatment), the voltage control section 312b controls the driving voltage, whereby the pressure of the exhaust channel (the pressure in the body cavity) is maintained at a desired suction pressure. Note that, during the suction treatment for the patient, the exhaust channel and the detection space S have the same pressure. Therefore, the gas that has flowed out from the outflow port 156a flows toward the suction pump 210 along the exhaust channel without flowing into the detection space S and is discharged to the outside by the suction pump 210.

That is, since the gas sucked from the body cavity of the patient does not flow into the control unit 300, it is possible to reuse the control unit 300 including the pressure sensor 316 after the end of the suction treatment.

The embodiment disclosed herein should be considered illustrative and not restrictive in all aspects. The scope of the present invention is indicated by claims rather than by the above explanation of the embodiment. Further, all changes in meanings and scopes equivalent to claims are included in the scope of the present invention.

For example, in the embodiment, the example is explained in which the volume changing section 140 has the shape such as to be accommodated on the inner side of the storing section main body 120 when the pressure in the storage space 110a is lower than the reference pressure and also when the pressure in the storage space 110a is about to rise to be equal to or higher than the reference pressure. However, the volume changing section 140 may be connected to the storing section main body 120 to be accommodated on the inner side of the storing section main body 120 when the pressure in the storage space 110a is lower than the reference pressure and to bulge to the outer side of the storing section main body 120 when the pressure in the storage space 110a is about to rise to be equal to or higher than the reference pressure. Alternatively, the volume changing section 140 may be connected to the storing section main body 120 to be located on the outer side of the storing section main body 120 when the pressure in the storage space 110a is lower than the reference pressure and when the pressure in the storage space 110a is about to rise to be equal to or higher than the reference pressure. Note that, in this case, when the pressure in the storage space 110a is lower than the reference pressure, the volume changing section 140 is in a deflated state to minimize the buffer space 140a thereof.

In the embodiment, the example is explained in which the volume changing section 140 is fixed to the storing section main body 120 via the inner plug 160 and the O-ring 170. However, the volume changing section 140 may be attached to the storing section main body 120 via an adhesive or the like or may be integrally molded with the storing section main body 120. In this case, the inner plug 160 and the O-ring 170 are omitted.

In the embodiment, the example is explained in which the attachment section 126 of the storing section main body 120 is provided in the upper part of the storing section main body 120. However, the attachment section 126 may be provided on the sidewall of the storing section main body 120.

In the embodiment, the example is explained in which the connecting member 220 includes the mounting section 236. However, the mounting section may be provided in the storage container 100. In this case, the mounting section is desirably provided in an upper part of the storage container 100 or the outer side surface of the water sealing section 150.

In the embodiment, the example is explained in which the suction pressure is set by the operation of the operation switch 317. However, a method of setting the suction pressure is not limited to this. For example, the substrate 312 may include a receiving section capable of receiving a signal from an external transmitter (remote controller, etc.) and may be configured to be capable of setting the suction pressure according to a signal from the transmitter. Alternatively, the storage container 100 may include a suction-pressure setting section capable of setting the suction pressure in addition to the storing section 110 and the water sealing section 150. The suction-pressure setting section includes a suction-pressure setting space linked to the suction space 154a and capable of setting the suction pressure. In the suction-pressure setting section, a communication pipe for causing the suction space 154a and the suction-pressure setting space and the external space to communicate is provided. The suction pressure is set according to an amount of liquid such as sterile distilled water injected into the suction-pressure setting space through the communication pipe.

In the embodiment, the example is explained in which the so-called diaphragm pump is used as the suction pump 210. However, the suction pump 210 may be a pump including a motor. In this case, for example, a tube is used as the connecting member 220. The suction port of the pump and the outflow section 156 may be connected by the tube.

The embodiment is generally explained below.

A storage container in this embodiment includes: a storing section including a storage space capable of storing liquid and including an inflow port for causing the liquid to flow into the storage space; and a water sealing section including a coupling space linked to the storage space and a suction space linked to a suction source, the water sealing section being capable of sealing the coupling space and the suction space off from each other with water. The storing section includes an inflow section connectable to a tube to allow the inflow port and the inner side of the tube to communicate and a volume changing section capable of changing the volume of the storage space. The volume changing section is deformed to increase the volume of the storage space when the pressure in the storage space is about to rise to be equal to or higher than a reference pressure set in advance and is deformed to reduce the volume of the storage space when the pressure in the storage space is about to drop to be lower than the reference pressure.

In the storage container, the volume changing section is deformed to change the volume of the storage space when the pressure in the storage space is about to rise to be equal to or higher than the reference pressure or when the pressure in the storage space is about to drop to be lower than the reference pressure. Therefore, the reference pressure is set to a value smaller than pressure generated in the storage space, for example, when the patient coughs, whereby the state of the storage space is suppressed from changing to the excessive positive pressure state and the excessive negative pressure state. Specifically, when a large amount (an amount larger than an amount involved in the respiration in the steady state) of gas temporarily flows into the storage space from the body cavity of the patient through the inflow port because, for example, the patient coughs, whereby the pressure in the storage space is about to rise to be equal to or higher than the reference pressure, the volume changing section is deformed to increase the volume of the storage space (to suppress the rise of the pressure in the storage space). Therefore, the state of the storage space is suppressed from changing to the excessive positive pressure state. After a large amount of gas temporarily flows into the storage space (after the patient coughs), when the gas flows out from the storage space to the outside of the storing section (into the body cavity of the patient) through the inflow port, whereby the pressure in the storage space is about to drop to be lower than the reference pressure, the volume changing section is deformed to reduce the volume of the storage space (suppress a decrease in the pressure in the storage space). Therefore, the state of the storage space is suppressed from changing to the excessive negative pressure state. Moreover, during the use of the storage container, the tube is connected to the inflow section and the water sealing section is sealed by water, whereby the storage space is blocked from the external space (the outdoor air) of the storing section. Therefore, the occurrence of infection between the patient and other people is suppressed. That is, in the storage container, a part of the storing section including the storage space blocked from the external space during use is the volume changing section capable of changing the volume of the storage space, and therefore the occurrence of infection between the patient and the other people and the occurrence of the excessive positive pressure state and the excessive negative pressure state of the storage space are suppressed.

In this case, it is preferable that the volume changing section has rigidity for maintaining, when the pressure in the storage space is equal to or lower than the reference pressure, a shape at a time when the pressure in the storage space is equal to the reference pressure.

Consequently, the reference pressure is set to a value smaller than pressure generated in the storage space, for example, when the patient coughs and higher than a range of pressure fluctuation in the storage space involved in respiration in the steady state of the patient, whereby the volume changing section is not deformed by respiration in the steady state of the patient. Therefore, for example, suction by a suction source is stopped, whereby a liquid surface of liquid encapsulated in the water sealing section moves up and down according to pressure fluctuation in the storage space involved in respiration in the steady state of the patient. Therefore, it is possible to check presence or absence of so-called respiratory movement while suppressing the state of the storage space from changing to the excessive positive pressure state and the excessive negative pressure state.

It is preferable that the storing section further includes a storing section main body having rigidity higher than the rigidity of the volume changing section, the volume changing section has a shape such as to be accommodated on the inner side of the storing section main body when the pressure in the storage space has reached the reference pressure and also when the pressure in the storage space is lower than the reference pressure, and the storing section main body has a shape such as to define the storage space between the inner surface of the storing section main body and the volume changing section.

Consequently, even in a case where the patient coughs, for example, in addition to the steady state, the volume changing section is accommodated on the inner side of the storing section main body having rigidity higher than the rigidity of the volume changing section, that is, the volume changing section is protected by the storing section main body, and therefore damage to the volume changing section is suppressed. Moreover, the occurrence of a deficiency such as a deficiency in which the deformation for increasing the volume of the storage space by the volume changing section is hindered by an obstacle or the like on the outer side of the storing section main body is prevented.

In this case, it is preferable that the volume changing section is connected to the storing section main body, and the storing section main body and the volume changing section includes a through-hole for causing a buffer space on the inner side of the volume changing section to communicate with the external space on the outer side of the storing section main body.

Consequently, since the volume changing section comes into contact with both of the storage space and the external spaced (e.g., the atmosphere), the reference pressure is set to any value smaller than the pressure generated in the storage space, for example, when the patient coughs and equal to or larger than the pressure in the external space (the atmospheric pressure), whereby the state of the storage space is suppressed from changing to the excessive positive pressure state and the excessive negative pressure state.

Further, in this case, it is preferable that the storage container further includes a lid section mountable on the storing section main body, and the lid section has a shape such as to suppress foreign substances from intruding into the buffer space from the external space through the through-hole and to allow circulation of gas between the external space and the buffer space.

Consequently, the deformation of the volume changing section is not hindered and intrusion of foreign substances from the external space into the buffer space in the volume changing section is suppressed.

The invention claimed is:

1. A storage container comprising:
a storing section including a storage space capable of storing liquid and including an inflow port for causing the liquid to flow into the storage space; and
a water sealing section including a coupling space linked to the storage space and a suction space linked to a suction source, the water sealing section being capable of sealing the coupling space and the suction space off from each other with water, wherein
the storing section includes an inflow section connectable to a tube to allow the inflow port and an inner side of the tube to communicate and a volume changing section capable of changing volume of the storage space, and
the volume changing section is deformed to increase the volume of the storage space when pressure in the storage space is about to rise to be equal to or higher than a reference pressure set in advance and is deformed to reduce the volume of the storage space when the pressure in the storage space is about to drop to be lower than the reference pressure, wherein:
the storing section further includes a storing section main body having rigidity higher than rigidity of the volume changing section,
the volume changing section is shaped to be accommodated on an inner side of the storing section main body when the pressure in the storage space reaches the reference pressure and also when the pressure in the storage space is lower than the reference pressure, and
the storing section main body is shaped to define the storage space between an inner surface of the storing section main body and the volume changing section.

2. The storage container according to claim 1, wherein the volume changing section has rigidity for maintaining, when the pressure in the storage space is equal to or lower than the reference pressure, a shape at a time when the pressure in the storage space is equal to or lower than the reference pressure.

3. The storage container according to claim 1, wherein
the volume changing section is connected to the storing section main body, and
the storing section main body and the volume changing section include a through-hole for causing a buffer space on the inner side of the volume changing section to communicate with an external space on an outer side of the storing section main body.

4. The storage container according to claim 3, further comprising a lid section mountable on the storing section main body, wherein
the lid section is shaped to suppress foreign substances from intruding into the buffer space from the external space through the through-hole and to allow circulation of gas between the external space and the buffer space.

* * * * *